US010665332B2

(12) United States Patent
Chan et al.

(10) Patent No.: US 10,665,332 B2
(45) Date of Patent: May 26, 2020

(54) SYSTEMS AND METHODS FOR FACILITATING PHYSIOLOGICAL DATA COLLECTION PRIOR TO APPOINTMENT

(71) Applicant: Elwha LLC, Bellevue, WA (US)

(72) Inventors: Alistair K. Chan, Bainbridge Island, WA (US); Jesse R. Cheatham, III, Seattle, WA (US); Joel Cherkis, Redmond, WA (US); Paul H. Dietz, Redmond, WA (US); Tom Driscoll, San Diego, CA (US); William Gates, Medina, WA (US); Roderick A. Hyde, Redmond, WA (US); Muriel Y. Ishikawa, Livermore, CA (US); Neil Jordan, Redmond, WA (US); Jordin T. Kare, San Jose, CA (US); Eric C. Leuthardt, St. Louis, MO (US); Nathan P. Myhrvold, Medina, WA (US); Patrick Neill, Sammamish, WA (US); Tony S. Pan, Bellevue, WA (US); Robert C. Petroski, Seattle, WA (US); David R. Smith, Durham, NC (US); Elizabeth A. Sweeney, Seattle, WA (US); Desney S. Tan, Kirkland, WA (US); Clarence T. Tegreene, Mercer Island, WA (US); David L. Tennenhouse, Hillsborough, CA (US); Yaroslav A. Urzhumov, Bellevue, WA (US); Gary Wachowicz, Lake Tapps, WA (US); Lowell L. Wood, Jr., Bellevue, WA (US); Victoria Y. H. Wood, Livermore, CA (US)

(73) Assignee: ELWHA LLC, Bellevue, WA (US)

( * ) Notice: Subject to any disclaimer, the term of this patent is extended or adjusted under 35 U.S.C. 154(b) by 1026 days.

(21) Appl. No.: 14/604,425

(22) Filed: Jan. 23, 2015

(65) Prior Publication Data
US 2016/0217259 A1  Jul. 28, 2016

(51) Int. Cl.
*G16H 10/60* (2018.01)
*G16H 50/20* (2018.01)
(Continued)

(52) U.S. Cl.
CPC ............. *G16H 10/60* (2018.01); *G16H 10/40* (2018.01); *G16H 40/20* (2018.01); *G16H 50/20* (2018.01)

(58) Field of Classification Search
CPC .... G06F 19/327; G06F 19/366; G06F 19/322; G06F 19/345; G16H 10/40; G16H 50/20;
(Continued)

(56) References Cited

U.S. PATENT DOCUMENTS 7,485,095 B2    2/2009  Shusterman
7,734,482 B1 *  6/2010  Vance ................... G06F 19/322
                                                                      705/3
(Continued)

OTHER PUBLICATIONS

Grunberger, et al., "Consensus Statement by the American Association of Clinical Endocrinologists/American College of Endocrinology Insulin Pump Management Task Force", Endocrine Practice, vol. 20 No. 5, May 2014, 463-89 (Year: 2014).*

(Continued)

*Primary Examiner* — Jonathan Durant
*Assistant Examiner* — Gregory D. Moseley
(74) *Attorney, Agent, or Firm* — Foley & Lardner LLP

(57) ABSTRACT

A method for facilitating physiological data acquisition includes scheduling a medical appointment between a patient and a medical provider. The medical appointment is to be conducted at a medical provider location on an appointment date. The method also includes selecting a medical device configured to acquire physiological data regarding the patient. The method further includes sending, to a fulfillment system, a request to provide the medical (Continued)

device to a patient location prior to the appointment date. The patient location is remote from the medical provider location.

33 Claims, 9 Drawing Sheets

(51) Int. Cl.
  *G16H 10/40* (2018.01)
  *G16H 40/20* (2018.01)
(58) Field of Classification Search
  CPC ........ G16H 10/60; G16H 40/20; G16H 20/60; G16H 20/00; G16H 20/30; G16H 50/30; G06N 20/00
  See application file for complete search history.

(56) References Cited

U.S. PATENT DOCUMENTS

| | | | |
|---|---|---|---|
| 7,860,725 B2 | 12/2010 | Gopinathan et al. | |
| 8,285,560 B2 | 10/2012 | Gopinathan et al. | |
| 2002/0059030 A1* | 5/2002 | Otworth | A61L 35/411 702/19 |
| 2003/0120135 A1 | 6/2003 | Gopinathan et al. | |
| 2004/0147818 A1 | 7/2004 | Levy et al. | |
| 2005/0075906 A1* | 4/2005 | Kaindl | G06F 19/327 705/2 |
| 2006/0122525 A1 | 6/2006 | Shusterman | |
| 2007/0156626 A1 | 7/2007 | Roehm et al. | |
| 2008/0208633 A1* | 8/2008 | Navani | G06F 19/322 705/3 |
| 2009/0144088 A1 | 6/2009 | Zubiller et al. | |
| 2011/0092825 A1 | 4/2011 | Gopinathan et al. | |
| 2011/0130746 A1* | 6/2011 | Budiman | A61B 5/14532 604/890.1 |
| 2011/0178820 A1* | 7/2011 | Soni | A61B 5/0002 705/3 |
| 2012/0143013 A1 | 6/2012 | Davis et al. | |
| 2013/0013333 A1 | 1/2013 | Gopinathan et al. | |
| 2014/0161667 A1* | 6/2014 | Kokic | G06F 19/327 422/68.1 |

OTHER PUBLICATIONS

Ramaiah et al., "Workflow and Electronic Health Records in Small Medical Practices", Perspectives in Health Information Management, Spring 2012, 16 pages.

* cited by examiner

SYSTEMS AND METHODS FOR FACILITATING PHYSIOLOGICAL DATA COLLECTION PRIOR TO APPOINTMENT

CROSS-REFERENCE TO RELATED APPLICATION

This application is related to U.S. application Ser. No. 13/930,928, titled "Medical Support System Including Medical Equipment Case," filed Jun. 28, 2013, which is incorporated herein by reference in its entirety.

BACKGROUND

Healthcare is a continuously evolving industry. Significant advancements have been made in research and technology, such as the development of ultra-portable and wearable medical devices. However, the full capabilities of such technologies are yet to be realized.

SUMMARY

One embodiment relates to a method for facilitating physiological data acquisition. The method includes scheduling a medical appointment between a patient and a medical provider. The medical appointment is to be conducted at a medical provider location on an appointment date. The method also includes selecting a medical device configured to acquire physiological data regarding the patient. The method further includes sending, to a fulfillment system, a request to provide the medical device to a patient location prior to the appointment date. The patient location is remote from the medical provider location.

Another embodiment relates to a method for facilitating physiological data acquisition. The method includes scheduling a medical appointment between a patient and a medical provider. The medical appointment is to be conducted at a medical provider location on an appointment date. The method also includes selecting a medical device configured to acquire physiological data regarding the patient. The method further includes sending, to a fulfillment system, a request to provide the medical device to a patient location prior to the appointment date. The patient location is remote from the medical provider location. Further yet, the method includes receiving the physiological data regarding the patient. In addition, the method includes performing a diagnostic evaluation for the patient. The diagnostic evaluation is based at least in part on the physiological data.

Another embodiment relates to a system for facilitating physiological data collection. The system includes a scheduler configured to receive a request for a medical appointment between the patient and a medical provider. The medical appointment is to be conducted at a medical provider location on an appointment date. The scheduler is also configured to schedule the medical appointment for the appointment date. The scheduler is further configured to select a medical device to acquire physiological data from the patient at a patient location prior to the appointment date. The patient location is remote from the medical provider location. Further yet, the scheduler is configured to schedule providing of the medical device to the patient location on a delivery date prior to the appointment date. The system also includes a fulfillment system configured to provide the medical device to the patient location on the delivery date. The system further includes a physiological data analyzer configured to receive and analyze the acquired physiological data from the medical device prior to the appointment date.

Another embodiment relates to a method for facilitating physiological data collection. The method is performed at a location remote from a patient location. The method includes receiving a request to schedule a medical appointment between a patient and a medical provider. The medical appointment is to be conducted at a medical provider location on an appointment date. The method also includes selecting a medical device configured to acquire physiological data regarding the patient. The method further includes providing the medical device to the patient location prior to the appointment date. The patient location is remote from the medical provider location. Further yet, the method includes receiving the physiological data regarding the patient. In addition, the method includes performing a diagnostic evaluation for the patient. The diagnostic evaluation is based at least in part on the physiological data. The method also includes transmitting the diagnostic evaluation to the medical provider.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
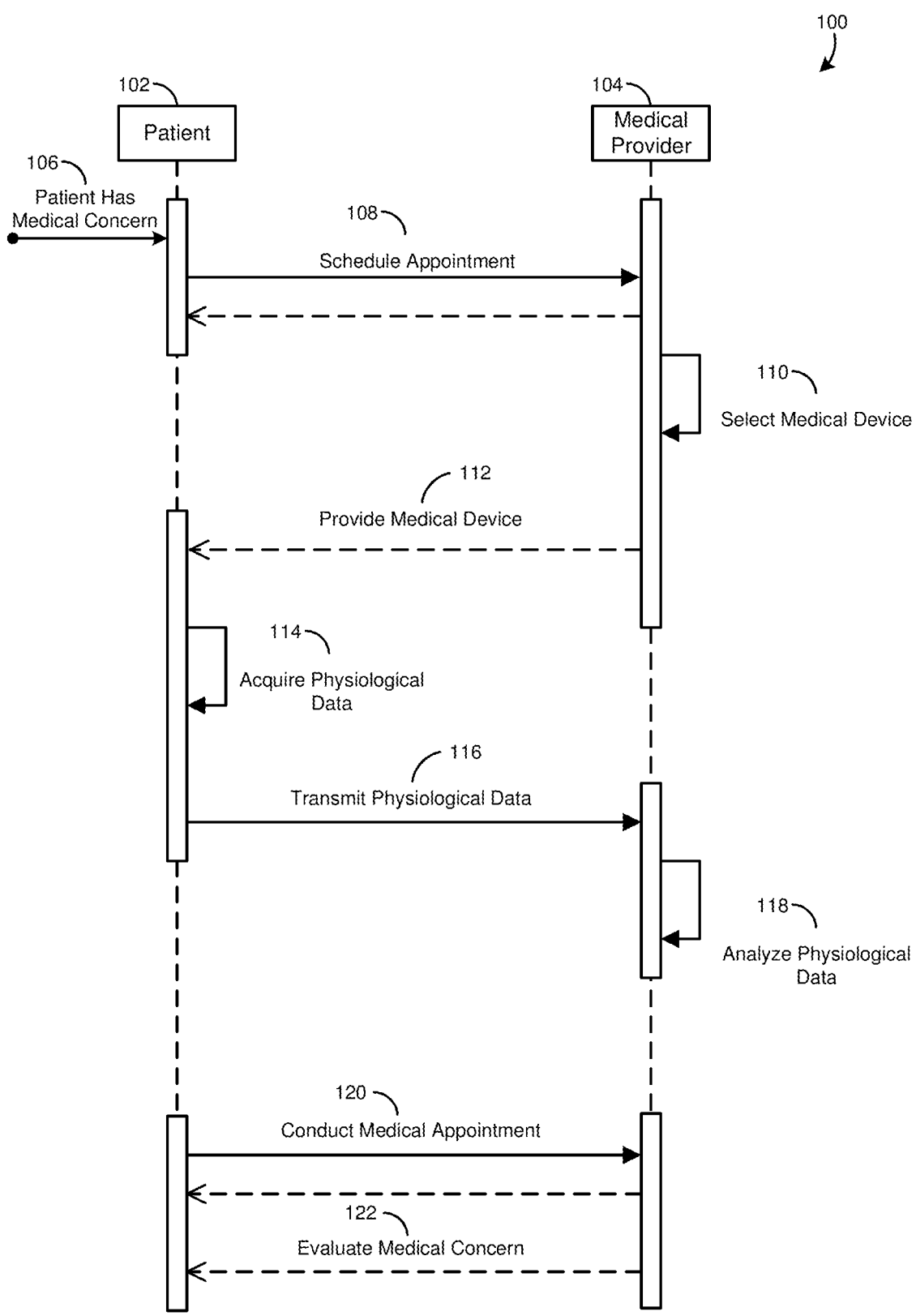
FIG. 1 is a sequence diagram of a workflow for diagnosing a non-emergency medical concern of a patient by a medical provider, according to an embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Conventional procedures for diagnosing non-emergency medical concerns of patients are often inefficient, time consuming, and inconvenient for patients. In a conventional workflow, a patient must typically travel to a medical provider at least two times, once for a preliminary evaluation appointment and again for a follow-up appointment. In some situations, the patient must also travel another time (e.g., to a diagnostic laboratory, a pharmacist, a specialist, etc.) to conduct treatment and/or further testing prescribed during the preliminary evaluation. In many situations, at least one of the appointments may be quite short and may require minimal contact between the patient and the medical provider. However, each of the appointments is a necessary hurdle that the patient must traverse in order for the patient's medical concern to be evaluated.

Various embodiments disclosed herein relate to an improved workflow for patient evaluation and diagnosis, including providing one or more medical devices to a patient in advance of a scheduled appointment to capture physiological data regarding the patient.

FIG. 1 is a sequence diagram of a workflow 100 of diagnosing a medical concern (e.g., a non-emergency medical concern) of patient 102 by medical provider 104, according to an embodiment. According to an embodiment as illustrated in FIG. 1, at 106, patient 102 has a medical concern. For example, patient 102 may be experiencing a pain in a particular body part or may generally feel ill. At 108, patient 102 contacts medical provider 104 to schedule a medical appointment regarding the medical concern. The medical appointment may be scheduled to be conducted on an appointment date. At 110, medical provider 104 selects a medical device. According to various embodiments and as explained in further detail below, the scheduling of the medical appointment and the selecting of the medical device at 110 may be based on any of various factors. In some implementations, the medical device is selected based on patient's 102 medical concern (e.g., an objective of the medical appointment). The scheduling of the medical appointment at 108 includes determining patient's 102 medical concern based on, for example, a preliminary interview between patient 102 and medical provider 104 as the appointment is being scheduled.

In some embodiments, the scheduling of the medical appointment and the selecting of the medical device are interdependent. For example, in some embodiments, the scheduling of the medical appointment is based on a measurement period required to acquire the physiological data by the medical device. The measurement period may vary depending on the particular selected medical device, patient's 102 medical concern, the level of evaluation required for patient 102, etc. For example, certain medical devices may require a single use (e.g., a single analyte collection or measurement), while other medical devices may require physiological data acquisition over a longer measurement period (e.g., for evaluating sleep patterns). In further embodiments, the selecting of the medical device is based on medical records (e.g., electronic medical records (EMR)) associated with patient 102. For example, patient's 102 medical records may include details regarding a previous diagnostic evaluation of patient 102.

In some embodiments, the scheduling of the medical appointment is based on a transit period. For example, the transit period may include at least one of a first time period required to provide the medical device to patient 102 and a second time period required to receive the medical device from patient 102. In further embodiments, the scheduling of the medical appointment is based on an analysis period required to analyze the physiological data. For example, certain implementations may require analysis by a diagnostic laboratory, while other implementations may automatically provide the necessary data to medical provider 104. In various embodiments, the scheduling of the medical appointment is based on an availability of medical provider 104 (e.g., availability of a clinician associated with medical provider 104 responsible for conducting the medical appointment). For example, a clinician's schedule may be accessed by the scheduling system to ensure that the clinician is available during the scheduled time of the appointment. In some implementations, the availability of the clinician is based on the particular medical concern of patient 102. For example, some clinicians perform certain procedures or work in certain offices depending on, for example, particular days of the week.

At 112, medical provider 104 provides the medical device to patient 102 before the appointment date. In some implementations, the providing of the medical device includes sending the medical device via post (e.g., U.S. Postal Service, United Parcel Service®, Federal Express®, etc.). In other implementations, the providing of the medical device includes patient 102 picking up the medical device from medical provider 104 or from another location. In some embodiments, medical provider 104 provides the medical device directly to patient 102. In other embodiments, medical provider 104 provides the medical device to patient 102 via a third-party, such as a fulfillment system. In further embodiments, the medical device is provided to patient 102 on a delivery date (e.g., at a particular time). For example, in certain implementations, the delivery date or the scheduling of delivery is triggered by data related to the medical appointment (e.g., an appointment date, transit period, analysis period, etc.), such that patient 102 receives the medical device with enough time to acquire the necessary physiological data prior to the appointment date.

According to various embodiments, medical provider 104 also sends usage instructions for the medical device to patient 102. Medical provider 104 may be configured to query a website or a manufacturer to receive the usage instructions. In some embodiments, the usage instructions are sent to patient 102 with the medical device. In further embodiments, the usage instructions are sent to patient 102 via a website. In further embodiments, the usage instructions are provided to patient 102 directly from the medical device (e.g., via a display on the medical device, such as an electronic display, or conveyed from the medical device via audible instructions).

In certain embodiments, the medical device is configured to detect proper usage and improper usage of the medical device by patient 102 (e.g., by querying the medical device). For example, in some embodiments, upon detecting improper usage by patient 102, the usage instructions including instructions to correct the improper usage are sent to patient 102 from the medical device. In further embodiments, the medical device provides a usage report to medical provider 104 that indicates at least one of proper and improper usage of the medical device. In some embodiments, medical provider 104 bases the scheduling of the appointment upon receipt of the usage report. For example, the appointment (or its actual date) may be set only after indication that the medical device was used properly (e.g., that valid physiological data has been obtained). In some embodiments, an appointment may be rescheduled or may be cancelled in response to an indication that the medical device was used improperly. For example, the appointment date may be delayed to allow time for improper usage to be corrected.

According to various embodiments, medical provider 104 also sends a usage schedule for the medical device to patient 102. For example, according to some implementations, the usage schedule is sent to patient 102 with the medical device, is sent to patient 102 via a website, or is sent to patient 102 from the medical device itself. In some embodiments, the usage schedule includes at least one of a predetermined number of measurements and a predetermined measurement period. In certain implementations, the usage schedule includes continuous measurements to be performed over the predetermined measurement period, or, alternatively, a predetermined number of measurements to be performed over the predetermined measurement period. In some embodiments, the medical device is configured to detect adherence to the usage schedule and deviation from the usage schedule. In some implementations, upon detecting a deviation from the usage schedule, the medical device is configured to notify at least one of patient 102 and medical provider 104 of the deviation. In some implementations, the medical device is configured to provide a usage report to medical provider 104 that indicates adherence to and deviation from the usage schedule. In some embodiments, medical provider 104 bases the scheduling of the appointment upon receipt of the usage report. For example, the appointment (or its actual date) may be set only after indication that the usage schedule was properly adhered to (e.g., that sufficient physiological data has been obtained). In some embodiments, an appointment may be rescheduled or may be cancelled in response to an indication of deviations from the usage schedule. For example, the appointment date may be delayed to allow time for complete physiological data to be collected, or for properly spaced data points to be collected.

At 114, upon receiving the medical device, patient 102 acquires physiological data using the medical device (e.g., using a diagnostic device of the medical device). As explained in further detail below, in some embodiments, the medical device includes a wearable sensor. In some implementations, the medical device includes an analyte storage device configured to collect and store analytes (e.g., blood, plasma, serum, saliva, urine, mucus, tears, semen, vaginal secretions, hair, skin, nucleic acid, stool, etc.). For example, in certain implementations, the medical device acquires physiological data from the analytes. Additionally or alternatively, in some implementations, the medical device stores the analytes for subsequent analysis.

At 116, the acquired physiological data is transmitted to medical provider 104. According to various embodiments, the physiological data is transmitted to medical provider 104 directly from the medical device, or the physiological data is first uploaded from the medical device to a client device (e.g., a computer), and is subsequently transmitted from the client device to medical provider 104. In some embodiments, the physiological data is transmitted via any of a wired or wireless connection. Further, in some embodiments, the physiological data is transmitted in real-time or near real-time (e.g., immediately upon the data being acquired), while in other embodiments, the physiological data is stored in memory and is subsequently transmitted to medical provider 104. In some embodiments, the physiological data is transmitted to at least one of a diagnostic laboratory and a third-party in addition to or instead of the data being transmitted directly to medical provider 104.

In some embodiments, patient 102 sends the medical device itself to at least one of medical provider 104, the diagnostic laboratory, and the third-party prior to the appointment date (e.g., via post or in-person delivery) or on the appointment date (e.g., during the medical appointment). In such embodiments, medical provider 104, the diagnostic laboratory, or the third-party can retrieve the physiological data from the medical device (e.g., the physiological data may be stored in memory (e.g., in a data storage device) on the medical device). In certain examples in which an analyte is stored by the medical device, medical provider 104, the diagnostic laboratory, the third-party, or the medical device itself retrieves and analyzes the analyte from the medical device.

At 118, at least one of medical provider 104, the diagnostic laboratory, the third-party, and the medical device itself analyzes the physiological data. According to various embodiments, the physiological data is analyzed prior to or on the appointment date (e.g., during the medical appointment). In some implementations, the physiological data is anonymized prior to being transmitted to the third-party.

In some embodiments, the medical appointment is canceled upon analyzing the physiological data. For example, it may be determined that the medical appointment is not necessary, based on the analysis. In an embodiment, the medical appointment may be canceled and rescheduled upon analyzing the physiological data. For example, the medical provider may provide a particular type of medical service (e.g., dermatology), and upon analyzing the physiological data, it may be determined that the patient should conduct a medical appointment with another medical provider that provides a different type of medical service (e.g., oncology). In some embodiments, a prescription (e.g., a prescription drug) may be prescribed based on the diagnostic evaluation. The prescription may be automatically sent to the patient or communicated to a pharmacist.

At 120, the medical appointment is conducted between patient 102 and medical provider 104. In some embodiments, the physiological data is utilized during the medical appointment. At 122, medical provider 104 evaluates patient's 102 medical concern. For example, medical provider 104 may diagnose the medical concern, prescribe further treatment or testing, explain the evaluation to patient 102, etc.

By sending the medical device to patient 102 and acquiring physiological data of patient 102 prior to the appointment date, workflow 100 of FIG. 1 facilitates the diagnosis of medical concerns more quickly, efficiently, conveniently, and effectively compared to conventional workflows. For example, workflow 100 provides advantages to patient 102 in that it involves less time and expense compared to conventional workflows because patient 102 is required to travel to medical provider 104 only once. In contrast, conventional workflows often require patients to travel to medical provider 104 at least twice—for a preliminary evaluation appointment and for a follow-up appointment—and possibly a third time (e.g., to a diagnostic laboratory, a pharmacist, a specialist, etc.) to conduct prescribed treatment and/or further testing. Therefore, workflow 100 allows patient 102 to save time associated with travel and waiting for clinician availability, as well as costs associated with travel and medical provider fees (e.g., insurance co-pays).

In addition, because medical provider 104 receives patient's 102 physiological data prior to the appointment date, medical provider 104 is able to perform an initial evaluation of patient's 102 medical concern without requiring an initial physical appointment between patient 102 and medical provider 104. Thus, workflow 100 of FIG. 1 improves medical provider's 104 efficiency, utilization of resources and staff, and cost-savings.

Figure 2:
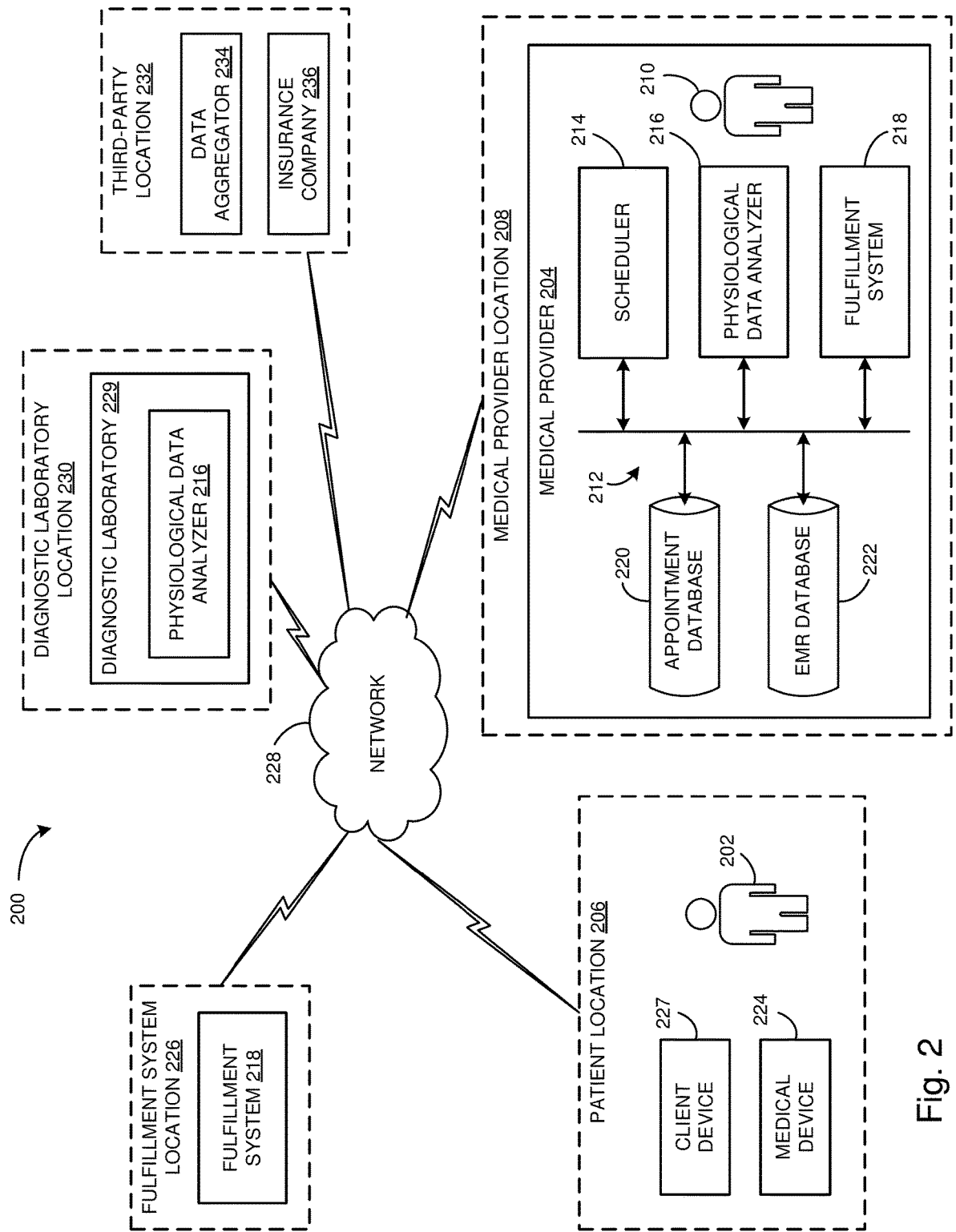
FIG. 2 is a block diagram of an example of patient medical diagnosis system, according to an embodiment.

FIG. 2 is a block diagram of an example of patient medical diagnosis system 200, according to an embodiment. For example, system 200 may be utilized in connection with workflow 100 of FIG. 1, in addition to other workflows and systems. System 200 includes patient 202 (e.g., similar to or same as patient 102 of FIG. 1), and medical provider 204 (e.g., same as or similar to medical provider 104 of FIG. 1). In certain implementations, medical provider 204 may be a hospital, a clinic, a doctor's office, etc. Patient 202 is located at patient location 206 and medical provider 204 is located at medical provider location 208 remote from patient location 206. Patient location 206 refers to a location in which patient 202 is typically located, such as patient's 202 residence. However, from time to time, patient 202 may travel to other locations, such as to medical provider location 208 for a medical appointment, for example.

Medical provider 204 includes clinician 210 (e.g., a doctor, a dentist, a nurse, a physician's assistant, a medical specialist, a caregiver, etc.). Medical provider 204 also includes medical information system 212, including scheduler 214, physiological data analyzer 216, fulfillment system 218, appointment database 220, and EMR database 222.

According to an embodiment, scheduler 214 is configured to receive a request for a medical appointment between patient 202 and medical provider 204. More specifically, the medical appointment is to be conducted between patient 202 and clinician 210 of medical provider 204 at medical provider location 208. In an example, a purpose of the medical appointment is to evaluate a medical concern of patient 202.

Upon receiving the request for the medical appointment, scheduler 214 is configured to schedule the medical appointment and to select medical device 224 to acquire physiological data from patient 202 at a patient location 206 prior to the appointment date. As described above in connection with workflow 100 of FIG. 1, the scheduling of the medical appointment and the selecting of medical device 224 may be based on any of various factors. For example, in some embodiments, scheduler 214 accesses appointment database 220 to determine availability of clinician 210 and other resources. In further embodiments, scheduler 214 accesses EMR database 222 to reference patient's 202 medical records, which also may affect the scheduling of the medical appointment and the selecting of medical device 224.

According to various embodiments, scheduler 214 schedules providing of medical device 224 to patient location 206 on a delivery date prior to the appointment date. The providing of medical device 224 may be based on any of various factors, such as a measurement period to acquire the physiological data, a transit period to provide medical device 224 to patient location 206 and to receive medical device 224 from patient location 206, an analysis period required for physiological data analyzer 216 to analyze the physiological data, etc.

According to various embodiments, fulfillment system 218 is configured to provide medical device 224 to patient location 206 on the delivery date determined by scheduler 214. In some embodiments, fulfillment system 218 is located at medical provider location 208. In some embodiments, fulfillment system 218 is located at diagnostic laboratory location 230. In other embodiments, fulfillment system 218 is located at fulfillment system location 226 (e.g., a mail order delivery outlet) remote from medical provider location 208. In these embodiments, medical information system 212 of medical provider 204 is in operative communication with fulfillment system 218 over network 228 (e.g., the Internet or an intranet).

According to various embodiments, physiological data analyzer 216 is configured to receive and analyze the acquired physiological data from medical device 224 prior to the appointment date. (e.g., prior to the day of the appointment, on the day of the appointment but prior to the appointment time, etc.). In some embodiments, physiological data analyzer 216 is configured to receive and analyze the acquired physiological data from medical device 224 during (or slightly after) the appointment. For example, physiological data analyzer 216 may be configured to retrieve an analyte sample from a medical device brought to the appointment by the patient, and then to analyze the analyte sample before completion of the appointment. The acquired physiological data is transmitted between patient location 206 and medical provider location 208 over network 228 via wired or wireless data communication or other communication methods. According to various embodiments, the physiological data is transmitted to medical provider 204 directly from medical device 224, or the physiological data is first uploaded from medical device 224 to client device 227 (e.g., a computer), and is subsequently transmitted from client device 227 to medical provider 204. Further, in some embodiments, the physiological data is transmitted in real-time or near real-time (e.g., immediately upon the data being acquired), while in other embodiments, the physiological data is stored in memory of medical device 224, and is subsequently transmitted to medical provider 204. In some embodiments, the physiological data is transmitted to diagnostic laboratory 229 in addition to or instead of the data being transmitted directly to medical provider 204.

The physiological data may be used by medical provider 204 (e.g., by clinician 210 of medical provider 204) to perform preliminary analysis or preliminary diagnosis on a medical concern of patient 202. According to various embodiments, system 200 is used, for example, in situations in which preliminary physiological data for patient 202 would assist medical provider 204 in analyzing a potential medical concern of patient 202 prior to an appointment between patient 202 and medical provider 204.

In some embodiments, scheduler 214 cancels the medical appointment upon the physiological data being analyzed. In an embodiment, the medical appointment may be canceled and rescheduled upon analyzing the physiological data. In some embodiments, physiological data analyzer 216 prescribes a prescription (e.g., a prescription drug) based on the diagnostic evaluation. Fulfillment system 218 may automatically send the prescription to patient location 206, or may automatically communicate to the prescription to a pharmacist.

By utilizing system 200, each of patient 202 and medical provider 204 may avoid needless medical appointments that consume time and resources of each of patient 202 and medical provider 204. In some embodiments, acquired physiological data, in addition to being used to analyze patient's 202 medical concern, is transmitted (e.g., over network 228) to third-party location 232, which may include data aggregator 234, insurance company 236, and other third-party locations 232. For example, the acquired physiological data may be used for various purposes, including billing, insurance claims, quality assurance, and data analytics, including individual or population studies of usage patterns, for example. Usage information may be linked to at least one of an identity of patient 202, clinician 210, or medical device 224, or anonymized, depending upon the intended use.

Figure 3:
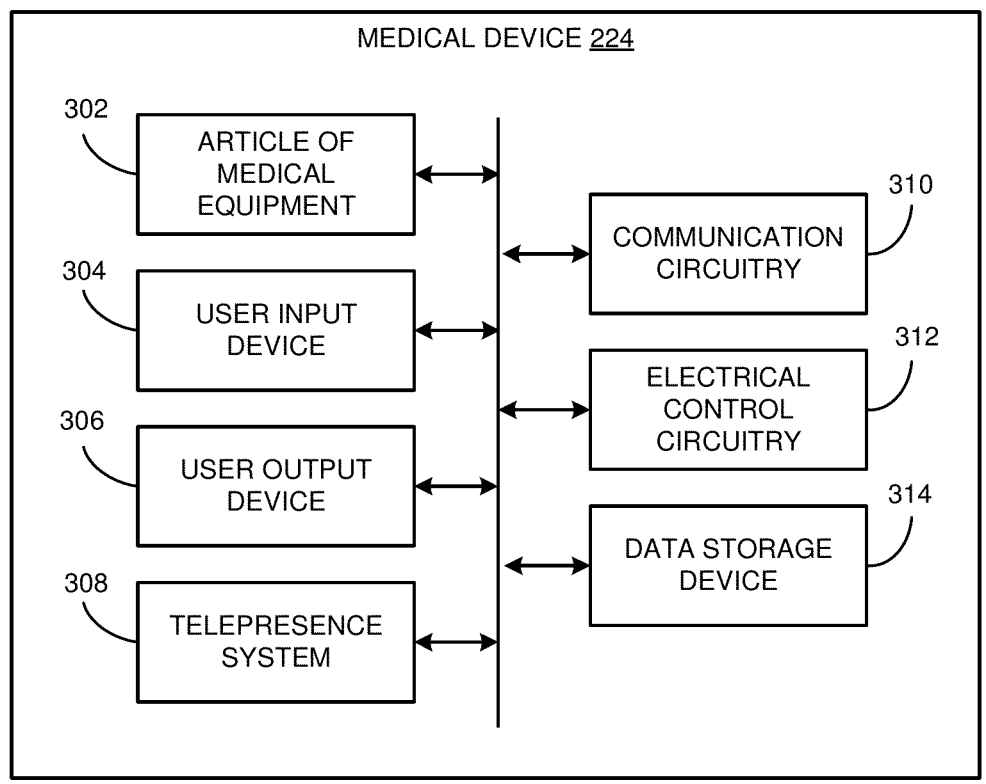
FIG. 3 illustrates block diagrams of the medical device and the physiological data analyzer of FIG. 2, according to an embodiment.
Figure 3:
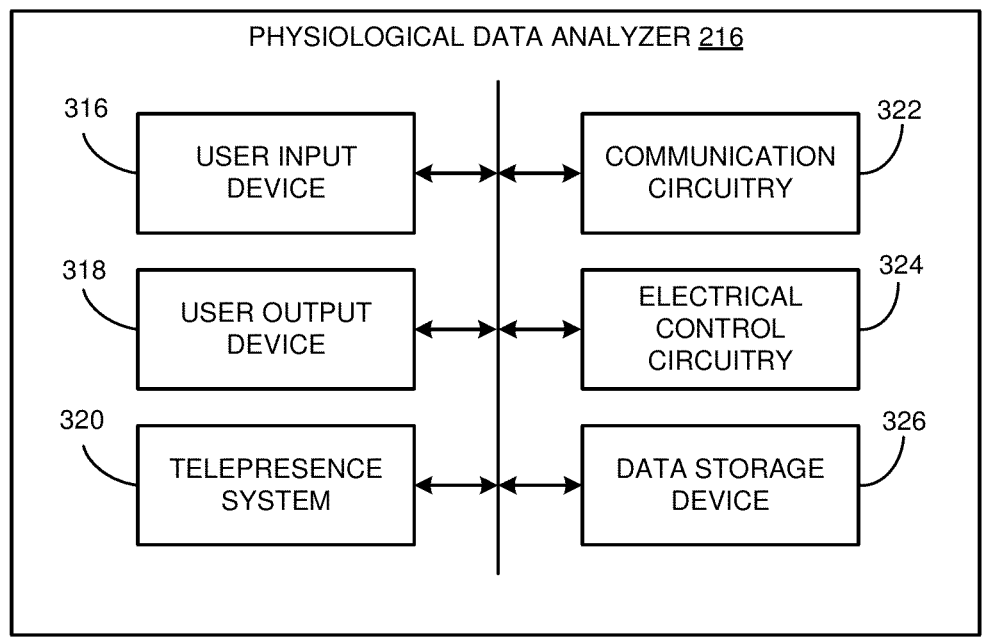

FIG. 3 includes block diagrams of medical device 224 and physiological data analyzer 216 of FIG. 2, according to various embodiments. As shown in FIG. 3, medical device 224 includes at least one article of medical equipment 302, first user input device 304, first user output device 306, first telepresence system 308, first communication circuitry 310, first electrical control circuitry 312, and first data storage device 314. Physiological data analyzer 216 includes second user input device 316, second user output device 318, second telepresence system 320, second communication circuitry 322, second electrical control circuitry 324, and second data storage device 326. First and second telepresence systems 308, 320, in combination with first and second communication circuitry 310, 322, facilitate communication of video, voice, text, and other types of communication between medical device 224 and physiological data analyzer 216.

Medical device 224 and physiological data analyzer 216 are communicatively coupled via respective first and second communication circuitry 310, 322 over network 228 (FIG. 2) via at least one of wired and wireless (e.g., cellular, satellite, Bluetooth, Wi-Fi, radio frequency, etc.) communication links. In some implementations, first and second communication circuitry 310, 322 are configured to transmit and/or receive at least one of operational mode data signals, usage data signals (e.g., including physiological data), identification data signals, telepresence signals, instructions, and queries between patient location 206 and medical provider location 208. In some implementations, first communication circuitry 310 is configured to transmit usage data signals (e.g., acquired physiological data) in near real-time (e.g., synchronous with acquiring the data). In other embodiments, acquired physiological data is stored in first data storage device 314, and first communication circuitry 310 is configured to receive the acquired physiological data from first data storage device 314 and to transmit the acquired physiological data in non-real-time (e.g., asynchronous with acquiring the data). In some implementations, first communication circuitry 310 transmits the acquired physiological data to at least one of medical provider 204 at medical provider location 208, diagnostic laboratory 229 at diagnostic laboratory location 230, and a third-party (e.g., data aggregator 234 and insurance company 236) at third-party location 232, as depicted in FIG. 2. Various device control signals, data signals, instructions, status signals, and the like may be transmitted between medical device 224 and physiological data analyzer 216 other than those explicitly recited herein.

In an embodiment, each of first and second electrical control circuitry 312, 324 includes a processor and memory. The processors may be implemented as a general-purpose processor, an application specific integrated circuit (ASIC), one or more field programmable gate arrays (FPGAs), a digital-signal-processor (DSP), a group of processing components, or other suitable electronic processing components. Memory includes one or more devices (e.g., RAM, ROM, Flash Memory, hard disk storage, etc.) for storing data and/or computer code (e.g., including or in addition to at least one of first and second data storage devices 314, 326) for facilitating the various processes described herein. Memory may be or include non-transient volatile memory or non-volatile memory. Memory may include database components, object code components, script components, or any other type of information structure for supporting the various activities and information structures described herein. Memory may be communicably connected to the processors and provide computer code or instructions to the processor for executing the processes described herein.

FIG. 3 depicts medical device 224 having a single article of medical equipment 302; however, it will be appreciated that, in various implementations, medical device 224 may include one, two, or more articles of medical equipment 302, without limitation. Furthermore, a single article of medical equipment 302 may be capable of performing a single function (e.g., detecting blood pressure), or may be capable of performing multiple functions (e.g., detecting blood pressure, heart rate, blood oxygenation, etc.).

Figure 4:
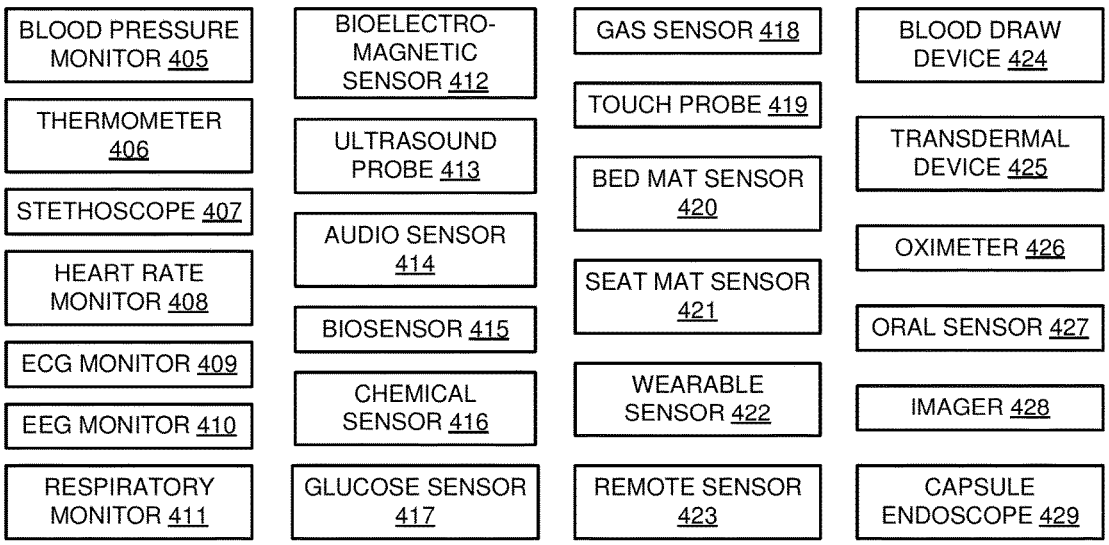
FIG. 4 is a block diagram of an article of medical equipment of the medical device of FIGS. 2 and 3, according to an embodiment.

FIG. 4 is a block diagram of article of medical equipment 302 of medical device 224, as shown generally in FIG. 3. Article of medical equipment 302 may include at least one of diagnostic device 402, analyte storage device 403, and medical treatment delivery device 404. Diagnostic device 402 may include, for example, at least one of blood pressure monitor 405, thermometer 406, stethoscope 407, a heart rate monitor 408, electrocardiogram (ECG) monitor 409, electroencephalogram (EEG) monitor 410, respiratory monitor 411, bioelectromagnetic sensor 412 for sensing one or more bioelectric or biomagnetic signals (including but not limited to electroencephalogram, electrocardiogram, electromyogram, electrooculogram, magnetic counterparts thereof, etc.), ultrasound probe 413, audio sensor 414, biosensor 415, chemical sensor 416 (e.g. for measuring chemicals or gases in bodily fluids or other samples (e.g., analytes) taken from the body or within the body), glucose sensor 417, gas sensor 418 (for measuring blood gases, expired gases, flatus, etc.) touch probe 419, bed mat sensor 420, seat mat sensor 421, wearable sensor 422, remote sensor 423, blood draw device 424 (e.g., syringe, finger stick, etc.), transdermal device 425 (e.g., for measuring subsurface tissue properties, for extracting analytes, etc.), oximeter 426 (e.g., a pulse oximeter for measuring arterial blood oxygen saturation ($SpO_2$) and pulse rate), oral sensor 427, imager 428, and capsule endoscope 429. Imager 428, for example, can be a camera, scanner or microscope, e.g., connected to a cell phone or other communication device. Imager 428 can be used, for example, to monitor balance, gait, or other whole body measurements, and/or to image skin (e.g., moles, imperfections, or lacerations).

In an embodiment, analyte storage device 403 is configured to store samples (e.g., analytes) taken from the body or within the body, including but not limited to blood, plasma, serum, saliva, urine, mucus, tears, semen, vaginal secretions, hair, skin, nucleic acid, stool, etc. In some embodiments, analytes are analyzed by diagnostic device 402 (e.g., by chemical sensor 420). In further embodiments, analytes are stored by analyte storage device 403 for subsequent analysis (e.g., by physiological data analyzer 216).

In an embodiment, medical treatment delivery device 404 includes a substance delivery device 428. Substance delivery device may include, for example, at least one of medication dispensing device 430 and transdermal delivery device 324. In an embodiment, medication dispensing device 430 is configured to dispense at least one formulated medication in response to a control signal (e.g., from the first electrical control circuitry 312). Medication dispensing device 430 may be, for example, a pill dispenser, or another device configured to dispense pills, capsules, powders, liquids, inhalants, suppositories, and other oral medications or inhalable medications. Medication dispensing device 430 may also deliver formulated medications for topical delivery, such as creams, ointments, eye drops, etc.

In an embodiment, transdermal substance delivery device 432, includes, for example, one or more of an injection device 434, a needle-based injection device 436, a needle-less injection device 438, an air gun 440, a jet injector 442, microneedles 444, a patch 446, or an infusion system 448 configured to deliver an infusible substance.

In an embodiment, medical treatment delivery device 404 is configured to deliver other types of treatments to patient 202, for example, including delivery of various forms of energy (light, electrical, magnetic, electromagnetic, acoustic, ultrasonic, thermal), pressure, vibration, or cooling (e.g., removal of energy), to produce various therapeutic effects in patient 202. Medical treatment delivery device 404 may include, for example, at least one of electrode 450, light source 452, electromagnetic field source 454, piezoelectric device 456, magnet 458, electromagnet 460, and heating element 462.

Figure 5:
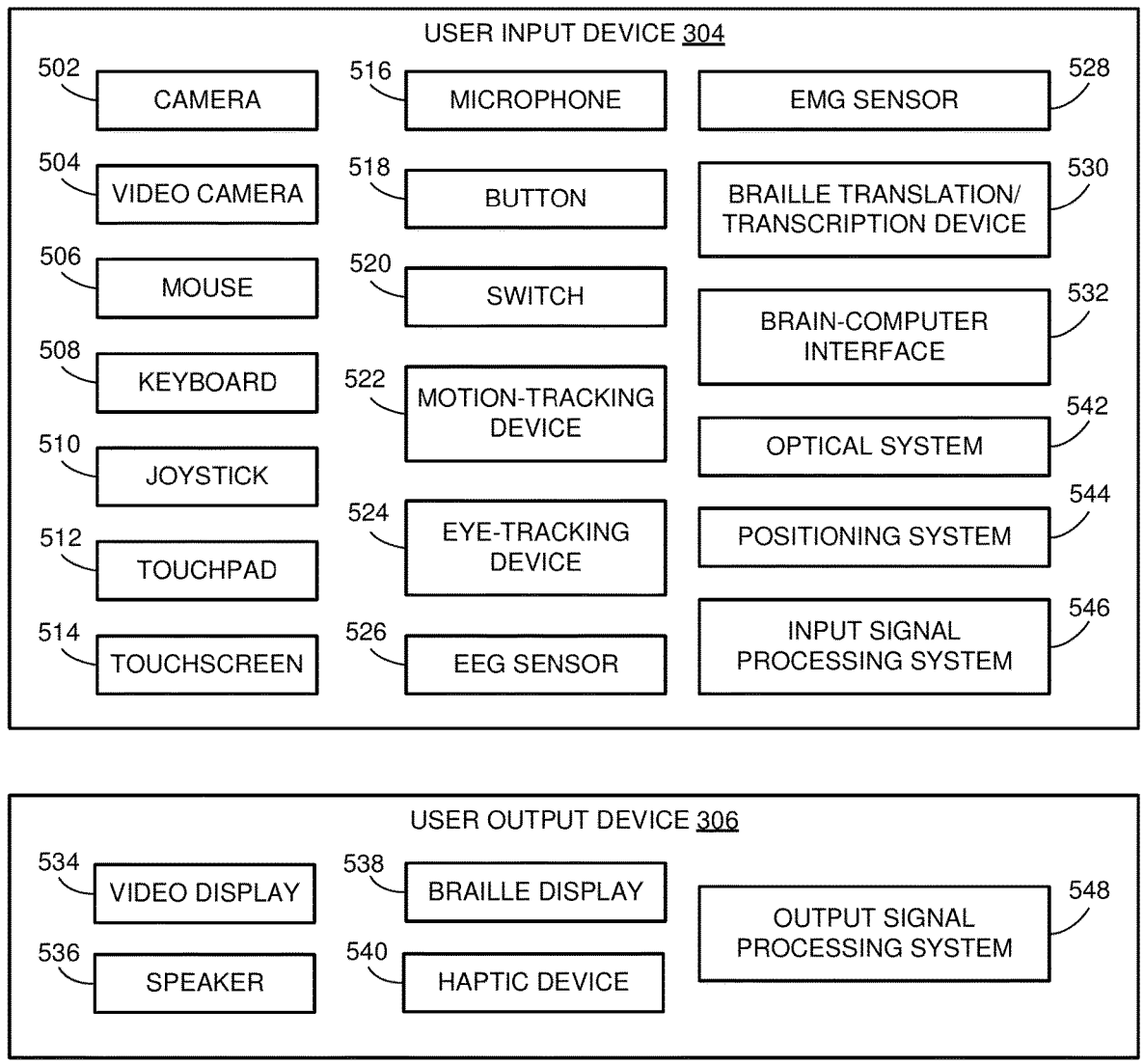
FIG. 5 is a block diagram illustrating user input and output devices of the medical device of FIGS. 2 and 3, according to an embodiment.

FIG. 5 is a block diagram of first user input and output devices 304, 306 of medical device 224 located at patient location 206. According to various embodiments, second user input and output devices 316, 318 of physiological data analyzer 216 located at medical provider location 208 may similarly include at least some of the components as described in connection with first user input and output devices 304, 306 as depicted in FIG. 5. First user input device 304 is adapted to accept a communication from a first user of medical device 224 (e.g., a patient or caregiver such as patient 202, as discussed herein above). First user output device 306 is adapted to present a communication to the first user (e.g., patient 202 at patient location 206). For example, the communication may be received from a second user at the monitoring location (e.g., clinician 210 at medical provider location 208). The communication signal from user input device 304 is transmitted to first communication circuitry 310 and/or first electrical control circuitry 312 (as depicted and described in connection with FIG. 3) for transmittal to second communication circuitry 322 at medical provider location 208 via a communication link. Communication signals originating from medical provider location 208 are provided to medical device 224 via first communication circuitry 310.

In some implementations, at least one of first and second user input devices 304, 316 includes at least one of a camera 502, a video camera 504, a mouse 506, a keyboard 508, a joystick 510, a touchpad 512, a touchscreen 514, a microphone 516, a button 518, a switch 520, a motion-tracking device 522, an eye tracking device 524, an EEG sensor 526, and EMG sensor 528, a braille translation/transcription device 530, and a brain-computer interface 532. In some implementations, at least one of first and second user output devices 306, 318 includes at least one of a video display 534, a speaker 536, a braille display 538, and a haptic device 540.

Any of first user input and output devices 304, 306 of medical device 224 and second user input and output devices 316, 318 of physiological data analyzer 216 may be configured as separately packaged devices configured to communicate with respective first and second electrical control circuitry 312, 324 via a wired connection (via a plug and jack or USB, for example) or wireless connection, or they may be built into or packaged with other system components. One or multiple of each of first and second user input devices 304, 318 and of each of first and second user output devices 306, 318 may be used, and they may be of the same or different types. For example, a conventional commercially available video camera (e.g., video camera 508) suitable for video conferencing can be used for audio/visual communication between patient 202 and medical provider 204 (e.g., via first and second telepresence systems 308, 320). In some implementations, the camera (e.g., camera 506 and/or video camera 508) is configured to provide audio/visual communication between patient 202 and medical provider 204 may also provide medically useful information. In some implementations, the camera (e.g., camera 506 and/or video camera 508) may function as article of medical equipment 302. In some implementations, two or more cameras (e.g., camera 506 and/or video camera 508) may be used to provide views of patient 202 from two or more different angles or positions. In some implementations, camera 506 and/or video camera 508 may be a specialized camera configured to obtain images for medical diagnostic purposes. For example, a specialized camera may produce images at a particular wavelength or range of wavelengths of light, have a higher spatial resolution or higher frame rate, or have other characteristics that permit it to obtain medically useful information. In some implementations, medical device 224 may include one or more photocell, charge-coupled device, scanner, 3D scanner, 3D imager, camera, single pixel camera, a visual camera, IR camera, a stereoscopic camera, a digital camera, a video camera, and a high speed video camera, for example. One or more digital images of the skin surface of patient 202 for use in generating a digital three-dimensional representation of the skin surface can be acquired from one or more of a digital camera or scanning device. For example, two video cameras 508, positioned slightly apart, can be used to image the same portion of skin surface of patient 202 in a process termed stereophotogrammetry. For example, a single camera 506 can be used to take multiple images under different lighting conditions or from different positions. In some implementations, the topography of the skin surface of patient 202 can be acquired in a point-cloud format using a three-dimensional sensing system consisting of two or more digital cameras and one or more projectors connected to a personal computer. In some implementations, at least one of first and second user input devices 304, 316 includes optical system 542, which may include one or more components such as reflectors, filters, polarizers, lenses, or shutters, which may be used to control various aspects of an image detected by respective first or second user input devices 304, 316. In some implementations, at least one of first and second user input devices 304, 316 includes a positioning system 544 including positioning components for adjusting and/or controlling the position, e.g. of camera 506 or video camera 508 in order to obtain a desired input. In some implementations, at least one of first and second user input devices 304, 316 includes input signal processing system 546 for performing filtering, amplification, and/or other processing of inputs received by respective first or second user input devices 304, 316. In some implementations, optical system 546, positioning system 548, and/or input signal processing system 550 are controlled by respective first or second electrical control circuitry 312, 324. Filtration, pan, tilt, or zoom may be controlled by adjustment of these and/or other controllable components, for example. At least one of first and second user input devices 304, 316 can also be used to receive input of other information from the corresponding user (e.g., patient 202 or clinician 210), either user-initiated or in response to a query. For example, patient 202 may be asked to provide inputs in response to questionnaires, tests of user ability or condition (e.g. test of vision, cognitive skills, motor skills), etc.

At least one of medical device 224 and physiological data analyzer 216 may also include respective first and second user output devices 306, 318, for providing information or feedback to a user (e.g., patient 202 or clinician 210), including video, graphic, or text displays, indicator lights, seven-segment displays, gauges, strip charts, auditory alarms, buzzers, voice outputs, tactile, haptic, or braille displays, electrical or magnetic stimulation devices, etc. In some implementations, at least one of first and second user output devices 306, 318 includes output signal processing system 548, for processing the output of respective first or second user output device 306, 318 prior to presentation of the output to corresponding patient 202 or clinician 210 as known by those having skill in the art, e.g. to provide amplification, filtration, or filtering of the signals produced by respective first or second user output device 306, 318.

Figure 6:
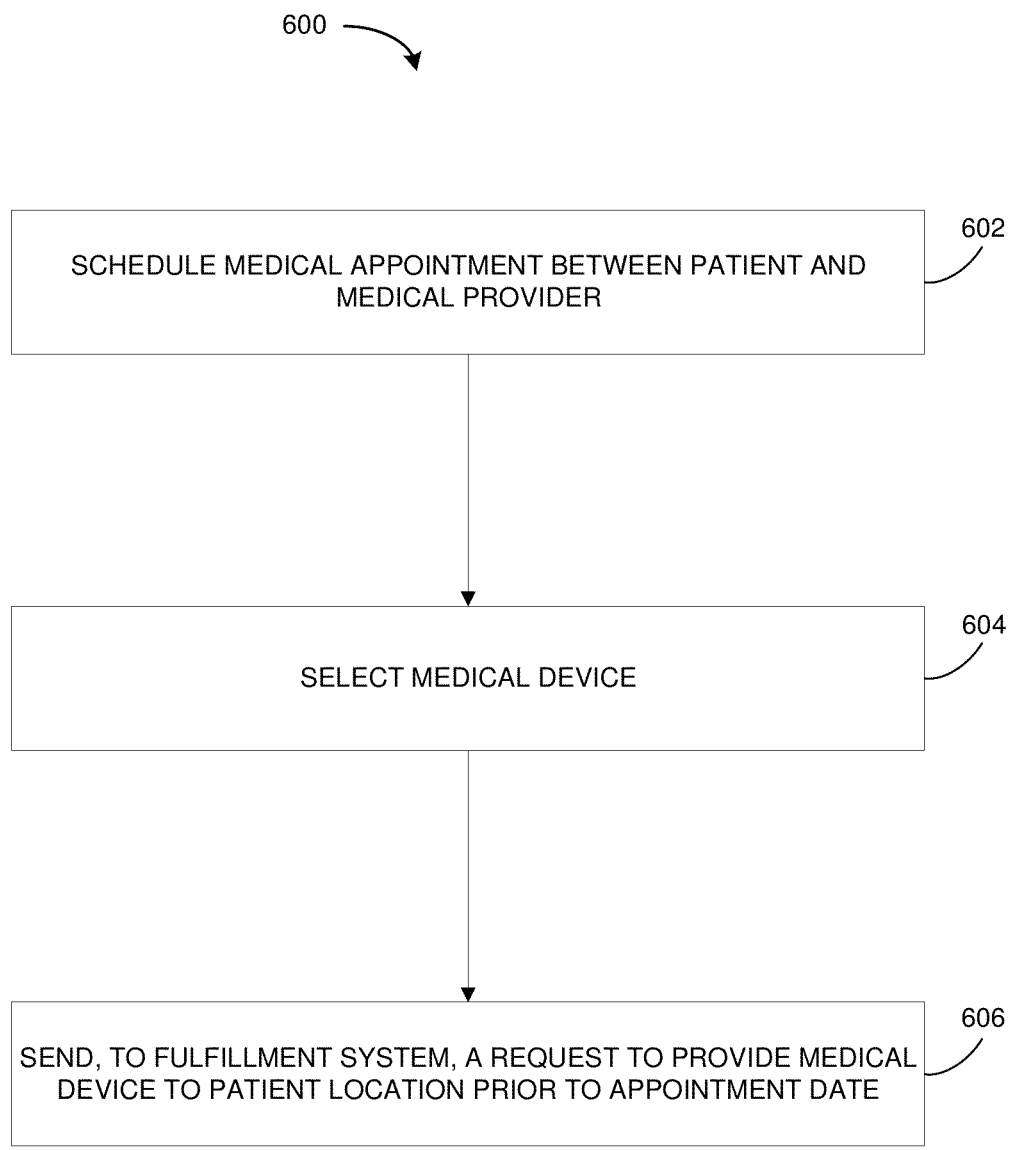
FIGS. 6-9 are flow diagrams illustrating methods of improved workflows for patient evaluation and diagnosis, according to an embodiment.

FIG. 6 is a flow diagram illustrating method 600 of an improved workflow for patient evaluation and diagnosis, according to an embodiment. According to an embodiment, method 600 includes providing one or more medical devices 224 to patient 202 in advance of a scheduled appointment to capture physiological data regarding patient 202. According to an implementation, method 600 is performed at least in part by medical provider 204 as depicted in FIG. 2. According to various embodiments, various factors, steps, and sub-steps relating to method 600 may include any of various factors, steps, and sub-steps, including but not limited to those described above in connection with any of workflow 100 of FIG. 1, system 200 of FIG. 2, and other systems, methods, and workflows.

At 602, a medical appointment is scheduled between patient 202 and medical provider 204. For example, in some implementations, patient 202 may have a medical concern and may contact medical provider 204 to schedule a medical appointment regarding the medical concern. The medical appointment may be scheduled to be conducted on an appointment date (e.g., at a specified day and time). In some implementations, the scheduler 214 of medical provider 204 as depicted in FIG. 2 schedules the medical appointment.

At 604, medical device 224 is selected. Medical device 224 may be configured to acquire physiological data regarding patient 202. In some implementations, the scheduler 214 of medical provider 204 as depicted in FIG. 2 selects medical device 224. In further implementations, fulfillment system 218 of at least one of medical provider location 208, fulfillment system location 226, and diagnostic laboratory location 230 as depicted in FIG. 2 selects medical device 224.

At 606, a request to provide medical device 224 to patient location 206 as depicted in FIG. 2 prior to the appointment date is sent to a fulfillment system. Patient location 206 may be remote from medical provider location 208 of medical provider 206, as depicted in FIG. 2. In some implementations, fulfillment system 218 of at least one of medical provider location 208, fulfillment system location 226, and diagnostic laboratory location 230 as depicted in FIG. 2 provides medical device 224.

Figure 7:
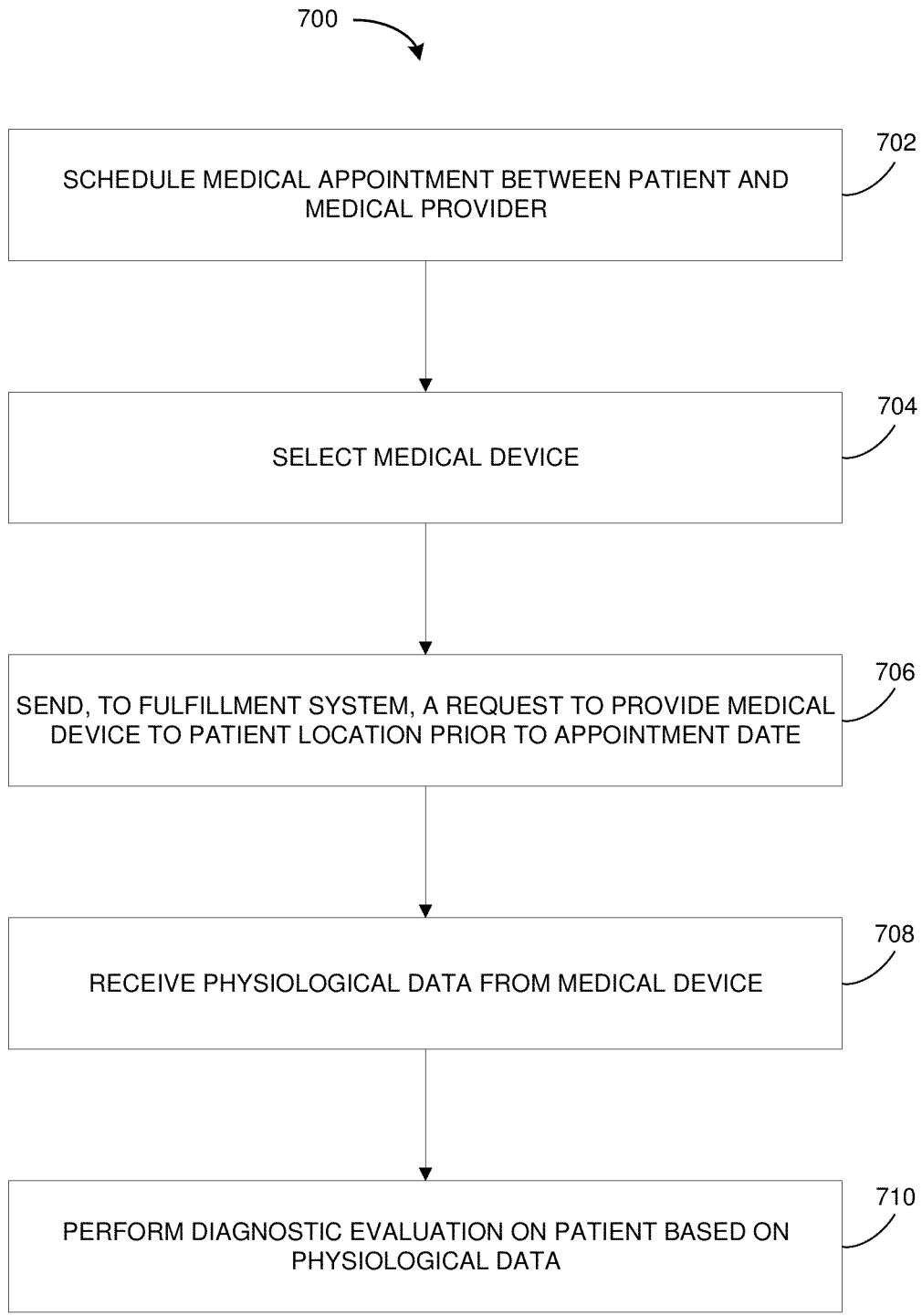

FIG. 7 is a flow diagram illustrating method 700 of an improved workflow for patient evaluation and diagnosis, according to an embodiment. According to an embodiment, method 700 includes providing one or more medical devices 224 to patient 202 in advance of a scheduled appointment to capture physiological data regarding patient 202. In some implementations, method 700 is performed at least in part by medical provider 204 as depicted in FIG. 2. According to various embodiments, various factors, steps, and sub-steps relating to method 700 may include any of various factors, including but not limited to those described above in connection with any of workflow 100 of FIG. 1, system 200 of FIG. 2, method 600 of FIG. 6, and other systems, methods, and workflows.

At 702, a medical appointment is scheduled between patient 202 and medical provider 204. For example, in some implementations, patient 202 may have a medical concern and may contact medical provider 204 to schedule a medical appointment regarding the medical concern. The medical appointment may be scheduled to be conducted on an appointment date. In some implementations, the scheduler 214 of medical provider 204 as depicted in FIG. 2 schedules the medical appointment.

At 704, medical device 224 is selected. Medical device 224 may be configured to acquire physiological data regarding patient 202. In some implementations, scheduler 214 of medical provider 204 as depicted in FIG. 2 selects medical device 224. In further implementations, medical device 224 is selected by fulfillment system 218 of at least one of medical provider location 208, fulfillment system location 226, and diagnostic laboratory location 230 as depicted in FIG. 2.

At 706, a request to provide medical device 224 to patient location 206 as depicted in FIG. 2 prior to the appointment date is sent to a fulfillment system. Patient location 206 may be remote from medical provider location 208 of medical provider 206, as depicted in FIG. 2. In some implementations, medical device 224 is provided by fulfillment system 218 of at least one of medical provider location 208, fulfillment system location 226, and diagnostic laboratory location 230 as depicted in FIG. 2.

At 708 physiological data is received from medical device 224. In some implementations, the physiological data is collected by medical device 224 at patient location 206, and the physiological data is transmitted by at least one of medical device 224 and client device 227 to at least one of medical provider 206, fulfillment system 218 at fulfillment system location 226, diagnostic laboratory 229, and a third-party (e.g., data aggregator 234, insurance company 236, etc.) at third-party location 232. In some implementations, the physiological data is received by physiological data analyzer 216 of at least one of medical provider 204 and diagnostic laboratory 229.

At 710, a diagnostic evaluation is performed on patient 202 at least in part based on the physiological data received at 708. In some implementations, the diagnostic evaluation is performed by physiological data analyzer 216 of at least one of medical provider 204 and diagnostic laboratory 229.

Figure 8:
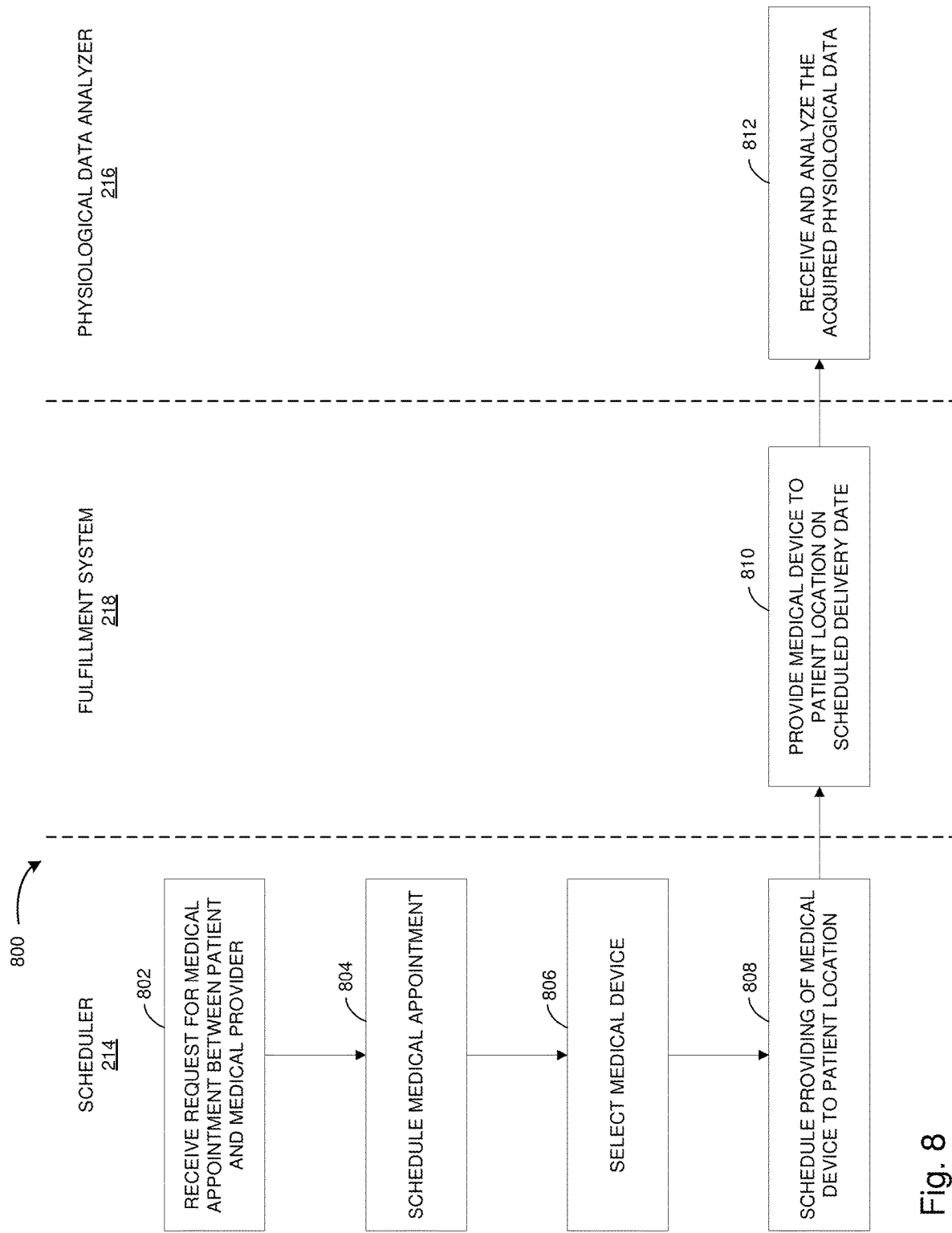

FIG. 8 is a flow diagram illustrating a method 800 of an improved workflow for patient (e.g., patient 202 of FIG. 2) evaluation and diagnosis, according to an embodiment. According to an embodiment, method 800 includes providing one or more medical devices 224 to patient 202 in advance of a scheduled appointment to capture physiological data regarding patient 202. In some implementations, method 800 is performed at least in part by at least one of scheduler 214 of medical provider 204; by fulfillment system 218 located at medical provider location 208, fulfillment system location 226, or diagnostic laboratory location 230; by physiological data analyzer 216 of at least one of medical provider 204 at medical provider location 208; and by diagnostic laboratory 229 at diagnostic laboratory location 230. According to various embodiments, various factors, steps, and sub-steps relating to method 800 may include any of various factors, including but not limited to those described above in connection with any of workflow 100 of FIG. 1, system 200 of FIG. 2, method 600 of FIG. 6, and other systems, methods, and workflows.

At 802, a request for a medical appointment between patient 202 and medical provider 204 is received by scheduler 214. At 804, a medical appointment is scheduled between patient 202 and medical provider 204 by scheduler 214 based on the request received at 802. The medical appointment may be scheduled to be conducted on an appointment date.

At 806, medical device 224 is selected by scheduler 214. Medical device 224 may be configured to acquire physiological data regarding patient 202 at patient location 206 prior to the appointment date. At 808, providing of medical device 224 to patient location 206 is scheduled by scheduler 218. The providing of medical device 224 may be scheduled to be performed on a delivery date prior to the appointment date.

At 810, medical device 224 is provided by fulfillment system 218 to patient location 206 on the delivery date scheduled at 808. At 812, the acquired physiological data is received and analyzed by the physiological data analyzer 216. Physiological data analyzer 216 may be located at medical provider 204 or at diagnostic laboratory 229. In an implementation, the physiological data may have been acquired by medical device 224 at patient location 206, and subsequently transmitted physiological data analyzer 216.

Figure 9:
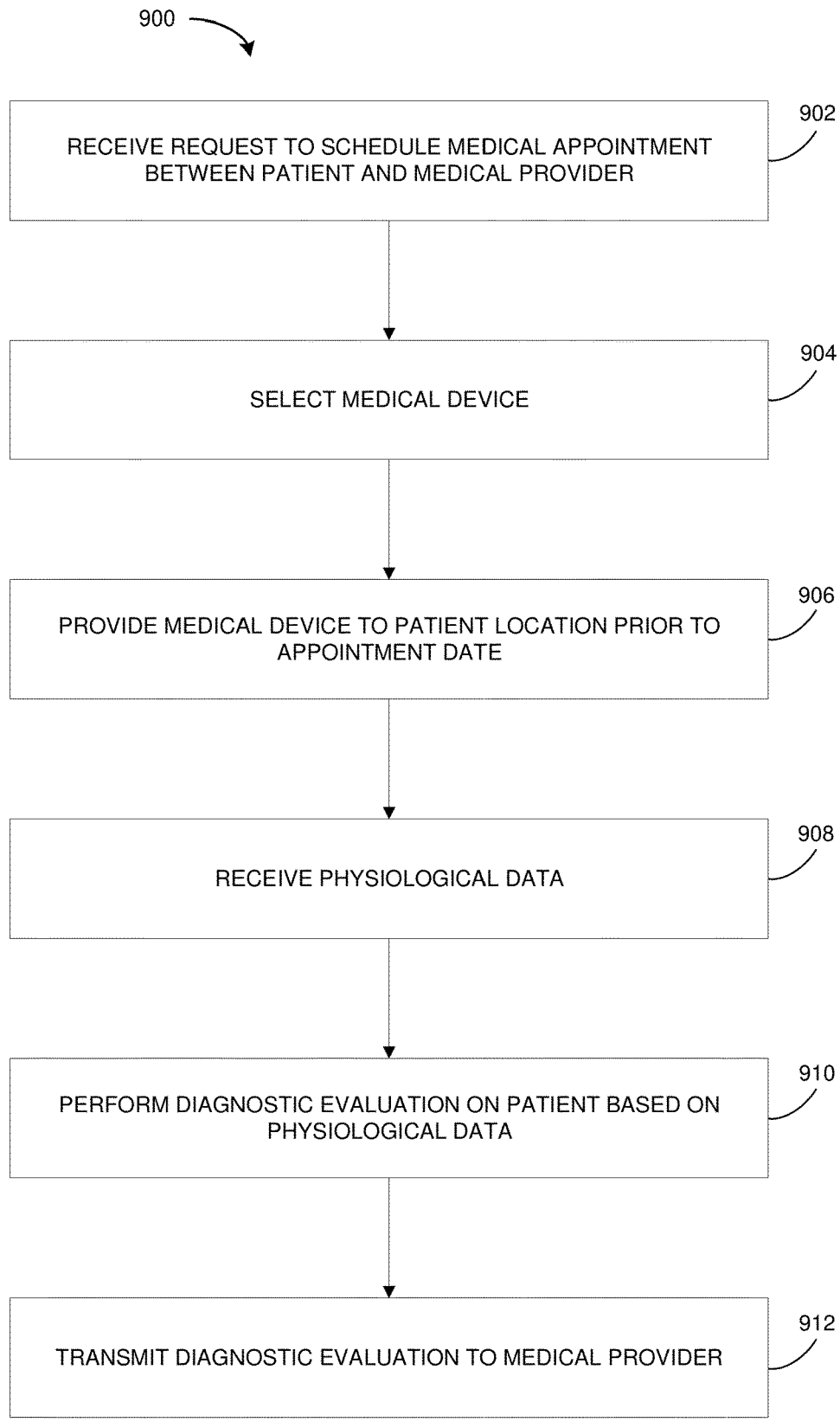

FIG. 9 is a flow diagram illustrating a method 900 of an improved workflow for a patient (e.g., patient 202 of FIG. 2) evaluation and diagnosis, according to an embodiment. According to an embodiment, method 900 includes providing one or more medical devices 224 to patient 202 in advance of a scheduled appointment to capture physiological data regarding patient 202. The method is performed at a location remote from patient location 206. In some implementations, method 900 is performed at least in part by at least one of medical provider 204, fulfillment system 218 of fulfillment system location 226, diagnostic laboratory 229 at diagnostic laboratory location 230, and a third-party (e.g., data aggregator 234, insurance company 236, etc.) as depicted in FIG. 2. In some embodiments, method 900 is performed entirely by medical provider 204. According to various embodiments, various factors, steps, and sub-steps relating to method 900 may include any of various factors, including but not limited to those described above in connection with any of workflow 100 of FIG. 1, method 600 of FIG. 6, system 200 of FIG. 2, and other systems, methods, and workflows.

At 902, a medical appointment is scheduled between patient 202 and medical provider 204. For example, in some implementations, patient 202 may have a medical concern and may contact medical provider 204 to schedule a medical appointment regarding the medical concern. The medical appointment may be scheduled to be conducted on an appointment date. In some implementations, the scheduler 214 of medical provider 204 as depicted in FIG. 2 schedules the medical appointment.

At 904, medical device 224 is selected. Medical device 224 may be configured to acquire physiological data regarding patient 202. In some implementations, the scheduler 214 of medical provider 204 as depicted in FIG. 2 selects medical device 224. In further implementations, fulfillment system 218 of at least one of medical provider 204 and fulfillment system location 226 as depicted in FIG. 2 selects medical device 224.

At 906, medical device 224 is provided to patient location 206 as depicted in FIG. 2 prior to the appointment date. As depicted in FIG. 2, patient location 206 may be remote from medical provider location 208 of medical provider 206. In some implementations, fulfillment system 218 of at least one of medical provider location 208, fulfillment system location 226, and diagnostic laboratory location 230 as depicted in FIG. 2 provides medical device 224.

At 908, physiological data regarding patient 202 is received. In various embodiments, the physiological data is received by at least one of physiological data analyzer 216 of at least one of medical provider 206 and diagnostic laboratory 229, by fulfillment system 218, and by at least one of data aggregator 234 and insurance company 236 at third-party location 232.

At 910, a diagnostic evaluation is performed on patient 202 based at least in part on received physiological data. In certain implementations, the diagnostic evaluation is performed by the device that received the physiological data at 908 (e.g., the at least one of physiological data analyzer 216, fulfillment system 218, and data aggregator 234, and insurance company 236). In further implementations, the diagnostic evaluation is performed by medical device 224 itself.

At 912, the diagnostic evaluation performed at 910 is transmitted to medical provider 204. In certain implementations, the diagnostic evaluation is transmitted to medical provider 204 by the device that received the physiological data at 908 (e.g., the at least one of physiological data analyzer 216, fulfillment system 218, and data aggregator 234, and insurance company 236). In further implementations in which the diagnostic evaluation is performed by medical device 224 itself, the diagnostic evaluation is transmitted to medical provider 204 by medical device 224. In further implementations, the diagnostic evaluation is entirely performed by medical provider 204 and is transmitted internally within medical provider 204.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various implementations and embodiments have been disclosed herein, other implementations and embodiments will be apparent to those skilled in the art. The various implementations and embodiments disclosed herein are for purposes of illustration and are not intended to be limiting, with the true scope and spirit being indicated by the following claims.

What is claimed is:

1. A method, comprising:
scheduling a medical appointment between a patient and a medical provider, the medical appointment to be conducted at a medical provider location on an appointment date;
selecting a medical device configured to acquire physiological data regarding the patient;
sending, to a fulfillment system, a request to provide the medical device to a patient location prior to the appointment date, the patient location being remote from the medical provider location, wherein the fulfillment system sends the medical device to the patient location prior to the appointment date in response to receiving the request;
sending usage instructions for the medical device to the patient, wherein the medical device is configured to detect proper usage and improper usage of the medical device by the patient;
causing the medical device to acquire the physiological data regarding the patient;
receiving a usage report from the medical device based on the acquired physiological data;
determining, using the usage report, that the usage report indicates improper usage of the medical device by the patient;
causing the medical device to continue to acquire physiological data regarding the patient in response to determining that the usage report indicates improper usage; and
canceling the medical appointment in response to determining that the usage report indicates improper usage.

2. The method of claim 1, further comprising:
receiving the physiological data from the medical device;
performing a diagnostic evaluation on the patient based on the physiological data.

3. The method of claim 2, wherein the medical provider is a first medical provider and wherein the medical appointment is a first medical appointment, and further comprising scheduling a second medical appointment with a second medical provider based on the diagnostic evaluation.

4. The method of claim 2, wherein the medical device is further configured to collect an analyte from the patient.

5. The method of claim 4, wherein the performing of the diagnostic evaluation is further based on the analyte.

6. The method of claim 4, wherein the medical device is configured to store the analyte for subsequent analysis.

7. The method of claim 1, further comprising:
receiving an analysis report from a diagnostic laboratory based on the physiological data; and
performing a diagnostic evaluation on the patient based on the analysis report.

8. The method of claim 1, wherein the scheduling of the medical appointment is based on a measurement period required to acquire the physiological data by the medical device.

9. The method of claim 8, wherein the measurement period is based on a medical concern of the patient.

10. The method of claim 1, wherein the scheduling of the providing is based on a measurement period required to acquire the physiological data by the medical device.

11. The method of claim 1,
further comprising sending a usage schedule for the medical device to the patient,
wherein the medical device is configured to detect adherence to and deviation from the usage schedule.

12. The method of claim 1, further comprising receiving, by the medical provider from the medical device, the physiological data acquired by the medical device.

13. A method, comprising:
scheduling a medical appointment between a patient and a medical provider, the medical appointment to be conducted at a medical provider location on an appointment date;
selecting a medical device configured to acquire physiological data regarding the patient;
sending, to a fulfillment system, a request to provide the medical device to a patient location prior to the appointment date, the patient location being remote from the medical provider location, wherein the fulfillment system sends the medical device to the patient location prior to the appointment date in response to receiving the request;
causing the medical device to acquire the physiological data regarding the patient;
receiving the physiological data regarding the patient;
performing a diagnostic evaluation for the patient, the diagnostic evaluation based at least in part on the physiological data;
receiving a usage report from the medical device based on the acquired physiological data;
determining, using the usage report, that the usage report indicates improper usage of the medical device by the patient;
causing the medical device to continue to acquire physiological data regarding the patient in response to determining that the usage report indicates improper usage; and
canceling the medical appointment in response to determining that the usage report indicates improper usage.

14. The method of claim 13, further comprising receiving an analysis report from a diagnostic laboratory based on the physiological data, wherein the performing of the diagnostic evaluation is based on the analysis report.

15. The method of claim 13, wherein the medical device is further configured to collect an analyte from the patient.

16. The method of claim 15, wherein the diagnostic evaluation is further based on the analyte.

17. The method of claim 15, wherein the medical device is configured to store the analyte for subsequent analysis.

18. The method of claim 13, wherein the scheduling of the medical appointment is based on a measurement period required to acquire the physiological data by the medical device.

19. The method of claim 13, further comprising sending usage instructions for the medical device to the patient, wherein the medical device is configured to detect proper usage and improper usage of the medical device by the patient.

20. The method of claim 19, wherein, upon detecting the improper usage by the patient, the usage instructions are sent to the patient from the medical device, the usage instructions including instructions to correct the improper usage of the medical device.

21. The method of claim 13, further comprising sending a usage schedule for the medical device to the patient, wherein the usage schedule identifies a predetermined measurement period, and wherein the usage schedule identifies a predetermined number of measurements to be acquired over the predetermined measurement period.

22. The method of claim 13, further comprising sending a usage schedule for the medical device to the patient, wherein the medical device is configured to detect adherence to and deviation from the usage schedule.

23. The method of claim 13, further comprising receiving, by the medical provider from the medical device, the physiological data acquired by the medical device.

24. A method performed at a location remote from a patient location, the method comprising:
- receiving a request to schedule a medical appointment between a patient and a medical provider, the medical appointment to be conducted at the medical provider location on an appointment date;
- selecting a medical device configured to acquire physiological data regarding the patient;
- providing the medical device to a patient location prior to the appointment date, the patient location being remote from the medical provider location;
- causing the medical device to acquire the physiological data regarding the patient;
- receiving the physiological data regarding the patient;
- performing a diagnostic evaluation for the patient, the diagnostic evaluation based at least in part on the physiological data;
- transmitting the diagnostic evaluation to the medical provider;
- receiving a usage report from the medical device based on the acquired physiological data;
- determining, using the usage report, that the usage report indicates improper usage of the medical device by the patient;
- causing the medical device to continue to acquire physiological data regarding the patient in response to determining that the usage report indicates improper usage; and
- canceling the medical appointment in response to determining that the usage report indicates improper usage.

25. The method of claim 24, wherein the medical device is further configured to collect an analyte from the patient.

26. The method of claim 25, wherein the diagnostic evaluation is further based on the analyte.

27. The method of claim 25, wherein the medical device is configured to store the analyte for subsequent analysis.

28. The method of claim 24, wherein the medical provider is a first medical provider and wherein the medical appointment is a first medical appointment, and further comprising scheduling a second medical appointment with a second medical provider based on the diagnostic evaluation.

29. The method of claim 24, wherein the scheduling of the medical appointment is based on a measurement period required to acquire the physiological data by the medical device.

30. The method of claim 24, wherein the scheduling of the providing is based on a measurement period required to acquire the physiological data by the medical device, and wherein the scheduling of the providing is further based on an analysis period required to analyze the physiological data.

31. The method of claim 24, further comprising sending usage instructions for the medical device to the patient, wherein the medical device is configured to detect proper usage and improper usage of the medical device by the patient.

32. The method of claim 31, further comprising providing a usage report to the medical provider, the usage report including an indication of at least one of the proper usage and the improper usage.

33. The method of claim 2, further comprising canceling the medical appointment based on the diagnostic evaluation.

* * * * *